United States Patent [19]

Landsberger

[11] Patent Number: 4,710,493

[45] Date of Patent: Dec. 1, 1987

[54] THERAPEUTIC AGENT FOR THE USE IN CANCER TREATMENT

[76] Inventor: Albert Landsberger, Lerchenweg 6, D-6901 Nussloch, Fed. Rep. of Germany

[21] Appl. No.: 640,661

[22] Filed: Aug. 14, 1984

[51] Int. Cl.[4] .................. A61K 31/725; A61K 31/70; A61K 31/66; A61K 37/54
[52] U.S. Cl. ........................................ 514/56; 514/62; 514/110; 424/94.63
[58] Field of Search ...................... 424/94; 514/56, 62, 514/110

[56] References Cited

FOREIGN PATENT DOCUMENTS 3220326 12/1983 Fed. Rep. of Germany .

OTHER PUBLICATIONS

Chem. Abst. 180: 45301y, 1984.

Primary Examiner—J. R. Brown
Assistant Examiner—John W. Rollins
Attorney, Agent, or Firm—Scully, Scott, Murphy & Presser

[57] ABSTRACT

Good results are obtained in the selective destruction of tumor cells when a glycosaminoglycan polysulfate, except heparin, is combined with a cytostatic drug. The known serious secondary effects of the cytostatic drugs are considerably reduced by the combination.

8 Claims, No Drawings

THERAPEUTIC AGENT FOR THE USE IN CANCER TREATMENT

This invention relates to a therapeutic preparation comprising a glycosaminoglycan polysulfate except heparin and at least one cytostatic drug besides other common carriers and companion substances.

The conventional methods known in the treatment of malignant tumors are substantially restricted to either surgical and/or radiological treatments as well as to the application of cytostatic drugs. The disadvantages of both the surgical and the radiological methods of treatment are known. When cytostatic drugs are applied in the treatment of malignant tumors both the malignant and the healthy tissue cells are damaged and thus, the narrow bounds of a therapy may also jeopardize the success of the treatment in this case.

It is true that "Journal of Medicinal Chemistry, 1974, vol. 17, No. 12, page 1335" teaches to increase the efficacy of the treatment of tumors with cytostatic drugs by simultaneously adding heparin. It has been noticed that patients who did not respond to the treatment with cytostatic drugs without heparin, responded better when heparin was used as an accompanying agent. However heparin is not the substance, either, for engendering affection of tumor cells preferably when there is an increased number of such cells which would mean, that preferably tumors in the advanced stage could be treated in a particularly efficacious manner.

Furthermore, one can proceed from the assumption that the problem of serious, unwanted secondary effects is not solved even if the glycosaminoglycan polysulfate heparin is added to common cytostatic drugs.

The task underlying this invention thus resides in providing a therapeutic preparation which has a selective and intensified effect on malignant tumor cells, in particular if there is already a great number of such cells. The preparation is meant to directly destroy these cells to a high degree without seriously affecting any healthy cells or healthy tissue.

This task is solved by the therapeutic preparation defined hereinbefore. With the aid of the combination according to the invention it is possible to selectively "open" the tumor cells (eg by damaging the membrane) and to concertedly introduced cytotoxically and cytolytically, respectively, effective substances, so that these substances are effective even if the tumor is already in an advanced stage of growth.

Glycosaminoglycan polysulfates also described as sulfated polyanions or formerly designated mucopolysaccharide polysulfuric acid esters are known from the therapy of various diseases. Substances counted among this family are, for example, heparins the coagulation characteristics of which have long been utilized. Other compounds of this class of substances are applied in the treatment of hyperlipoidaemiae and hypercholesteraemiae (eg heparins and heparinoids) or they are used as an antiarthritic (eg extracts of cartilage and chondroitin polysulfate). Furthermore, the substances observed have been known to distinctively and specifically inhibit enzyme systems (Schaffrath et al. in: Hoppe-Seylers Z. Physiol. Chem. 357, 499 (1976)). Investigations of biocytocultures revealed that—after incubation—malignant cells accumulate and store glycosaminoglycan polysulfates in a more intensive manner than benign cells.

Intensified accumulation of glycosaminoglycan polysulfate results in an inhibition of enzyme systems and thus, in an inhibition of biosynthetic performances in the cell metabolism of malignant cells. Hence a synergistic effect occurs in addition to the effect of the cytostatic drugs simultaneously applied, thus permitting that the latter can be used in concentrations which do either not or only slightly impair benign cells.

Comparative investigations between heparin and other glycosaminoglycan polysulfates, in particular chondroitin polysulfate have shown that the mode of action of glycosaminoglycan polysulfates can indeed be different. It has turned out that glycosaminoglycan polysulfates other than heparin are particularly characterized by an intensified effect occurring whenever the tumors already have a great number of cells. Though there is no final scientific explanation for this selective mode of behaviour, it is assumed that both kind and degree of sulfation are responsible for the phenomenon observed.

It has been absolutely surprising that glycosaminoglycan polysulfates other than heparin would show this particularly advantageous mode of action.

According to the invention the following substances can be applied as cytostatic drugs: alkylating cytostatic drugs such as nitrogen mustard derivatives and ethyleneimine derivatives, antimetabolites such as methotrexate, antagonists of purine and pyrimidine bases, cytostatically effective antibiotic agents and alkaloids such as cholchicine or vincristin.

In accordance with the invention preferably chondroitin polysulfate is used as glycosaminoglycan polysulfate.

Furthermore, the task underlying the invention is solved by adding the proteolytic enzyme trypsin to the therapeutic preparation.

The general biochemical expert knowledge includes that the effect of both substances is cancelled to a certain degree by the proteolytic enzyme trypsin because of interaction with glycosaminoglycan polysulfates. Owing to these experiences the person skilled in the art has not been able to continue his work within the meaning of the present invention. Because of reciprocities between all substances used according to the invention, which have still not entirely been understood, it is not an inhibiting effect that occurs but—in an absolutely unexpected manner—a synergistic one, as will be shown by the experiments of the present patent application.

Literature describes trypsin as cytolytic substance. It selectively attacks the malignant cell which has been already affected by additional application of a glycosaminoglycan polysulfate.

Addition of trypsin is important because there are biologically different resistant species also within one tumor cell family. Such resistant tumor cells are enzymatically partially digested to permit the cytostatic drugs to become effective. Trypsin therefore increases the selective effect of the preparation according to the invention to malignant cells and thus enables concerted application of tiny doses of cytostatic drugs which would affect all cells if solely these drugs were applied in much larger therapeutic doses.

The tumor cells are selectively "opened" by the glycosaminoglycan polysulfate, if desired, together with trypsin, with cytotoxically and cytolytically, respectively, effective substances being concertedly introduced.

The preparation according to the invention can parenterally be given.

The therapeutic individual dose of the therapeutic preparation ranges between 5 and 500 mg.

The quantity ratio of glycosaminoglycan polysulfate to cytostatic drugs ranges between 10:1 and 1:10 with regard to parts by weight of the active substances.

The quantity of cytostatic drugs depends on the kind of cytostatic drugs used.

The invention is explained by the following experiments. The following pharmacological active substances have been applied in these experiments:

(a) glycosaminoglycan polysulfates 1. chondroitin polysulfate
polysulfated chondroitin of bovine tracheal cartilage; disaccharide units consisting of D-glucuronic acid and N-acetyl galactosamine;
S-content: 13.2%
hexosamine: 103 μmol/100 mg, thereof approximately 89% of galactosamine
glucuronic acid: 97.3 μmol/100 mg 2. heparin-sodium
S-content: 10.0%
hexosamine: 152 μmol/100 mg (glucosamine: 145 μmol/100 mg, galactosamine: 0.02 μmol/100 mg)
uronic acid: 132 μmol/100 mg (b) cytostatic drugs cyclophosphamide

EXPERIMENT 1

72 homosexual rats (Sprague Dawley) were randomized in 6 groups. The individual groups were treated with the following active substances:
Group A: sodium heparin+cyclophosphamide
Group B: sodium heparin
Group C: chondroitin polysulfate+cyclophosphamide
Group D: chondroitin polysulfate
Group E: cyclophosphamide
Group F: control For tumor transmission each animal was inoculated with 20,000 cells of a yoshida-ascites-sarcoma.

The rats were given the following doses of the active agents (per kg rat):
cyclophosphamide: 25 mg/kg
sodium heparin: 10 mg/kg
chondroitin polysulfate: 10 mg/kg Therapy started 24 hours after the tumor had been communicated.

Temporal sequence of the experiment:
1. Application of the therapeutically active substances 24 hours after ascites inoculation;
2. application of the therapeutically active substances 28 hours after ascites inoculation;
3. application of the therapeutically active substances 72 hours after ascites inoculation.

3 weeks after the last application the results of the experiment were evaluated.

A table has been drawn up of the results:

TABLE 1

| group with 12 animals | alive | free from a tumor | dead | having a tumor |
|---|---|---|---|---|
| A | 11 | 11 | 1 | 1 |
| B | 1 | 1 | 11 | 11 |
| C | 11 | 11 | 1 | 1 |
| D | 0 | 0 | 12 | 12 |
| E | 2 | 2 | 10 | 10 |
| F | 0 | 0 | 12 | 12 |

EXPERIMENT 2

12 female rats (Sprague Dawley) were randomized in 2 groups.

For tumor transmission each animal was inoculated with 20,000 cells of a Yoshida-ascites-sarcoma.

The rats were given the following doses of the active substances (per kg rat):
cyclophosphamide: 25 mg/kg
sodium heparin: 10 mg/kg
chondroitin polysulfate: 10 mg/kg Start of the therapy: 48 hours after tumor transmission.

After the first application given 48 hours after the tumor had been communicated six further applications followed.

Group A. of the animals was treated with sodium heparin+cyclophosphamide.

Group B. of the animals was treated with chondroitin polysulfate+cyclophosphamide. A table 2 has been drawn up of the results.

TABLE 2

| Group with 12 animals | alive | free from a tumor | dead | having a tumor |
|---|---|---|---|---|
| a. | 2 | 2 | 10 | 9 |
| b. | 8 | 6 | 4 | 3 |

It definitely emerges from the results of both experiments 1 and 2 that chondroitin polysulfate acts on malignant cells in a surprisingly better manner if there is already an increased number of such cells. Equally good effect is achieved by the addition of heparin and chondroitin polysulfate in case the substances are applied very early, that is, at least 24 hours after the tumor has been communicated. Chondroitin polysulfate obviously causes cytostatic drugs to be incorporated also when the cells are in their resting stage. Cytostatic drugs alone and cytostatic drugs and heparin, respectively, destroy tumor cells almost only in a mitotic stage that is, in a phase when the cells are divided. Cytostatic drugs and heparin are only slightly superior to cytostatic drugs alone.

In a first clinical application extending over a period of 18 months the two-substance combination glycosaminoglycan polysulfate, except heparin, and cytostatic drug was tested on 125 persons suffering from various tumors such as, for example, carcinoma of the breast, gastrointestinal carcinoma, bronchial carcinoma, melanoma and cancer of the ovary. In addition to the particular effectiveness to tumors having a great number of cells, it has moreover been observed—and this is a very decisive innovation—that the known, considerable secondary effects of the cytostatic drugs (mitomycin, endoxan, vincristin, adriblastin) could be clearly reduced. Above all, younger women did either not or only slightly suffer from loss of hair. Generally there was no sickness, no vomiting and no diarrhoea. What has to be particularly emphasized is the fact, that the injuries of the medulla of a bone caused by cytostatic drugs could be remarkably reduced.

Both subjective and objective, negative secondary effects of the sole chemotherapy of cancer are thus either reduced or cancelled by adding a glycosaminoglycan polysulfate, except heparin, to a cytostatic drug, with a decisive improvement of the effect to malignant tumors being simultaneously achieved.

All effects of the described combination of active substances according to the invention which have been mentioned hereinbefore, constitute significant innovations hitherto unknown but extraordinarily important for the treatment of malignant tumors.

EXPERIMENT 3

36 female rats (Sprague Dawley) were divided into 3 groups. The animals were assigned to the groups according to the usual randomization.

Kind of tumor: Yoshida-ascites (haemorrhagic)
Number of cells of Yoshida-ascites inoculation: approximately 20,000
Beginning of the therapy: 48 hours (!) after the tumor has been inoculated.

Group A: chondroitin polysulfate + trypsin
Group B: chondroitin polysulfate + trypsin + cyclophosphamide
Group C: control Doses of the pharmacological active substances:
chondroitin polysulfate: 12 mg/kg
trypsin: 6 mg/kg
cyclophosphamide: 26 mg/kg
Temporal sequence of the experiment:
1. Application of the therapeutically active substances 48 hours after ascites inoculation;
2. application of the therapeutically active substances 3 days after ascites inoculation;
3. application of the therapeutically active substances 4 days after ascites inoculation.
4. application of the therapeutically active substances 6 days after ascites inoculation;
Testing of the efficacy: 21 days after the Yoshida-ascites tumor has been inoculated.

A table 3 has been drawn up of the results.

TABLE 3

| Group with 12 animals | alive | free from a tumor | dead | having a tumor |
|---|---|---|---|---|
| A | 7 | 0 | 5 | 5 |
| B | 8 | 8 | 4 | 4 |
| C | 0 | 0 | 12 | 12 |

EXPERIMENT 4

Experiment 3 was partly repeated. 36 female rats (Sprague Dawley) were divided into 3 groups. The animals were assigned to the groups according to the process of randomization.

Kind of tumor: Yoshida-ascites (haemorrhagic)
Number of cells upon tumor inoculation: 20,000
Beginning of the therapy: 2 days after tumor inoculation

| Group A: | chondroitin polysulfate + | 12 mg/kg |
| | trypsin + | 8 mg/kg |
| | cyclophosphamide | 26 mg/kg |
| Group B: | control | |
| Group C: | cyclophosphamide | 26 mg/kg |

1. Application of the therapeutically active substances 2 days after tumor transmission (20,000 cells of the Yoshida-ascites-scarcoma);
2. application of the therapeutically active substances 3 days after tumor transmission;
3. application of the therapeutically active substances 5 days after tumor transmission;
4. application of the therapeutically active substances 7 days after tumor transmission.

Examination of the test results after 21 days.
A table 4 has been drawn up of the results.

TABLE 4

| Group with 12 animals | alive | free from a tumor | dead | having a tumor |
|---|---|---|---|---|
| A | 9 | 9 | 3 | 3 |
| B | 0 | 0 | 12 | 12 |
| C | 2 | 2 | 10 | 10 |

EXPERIMENT 5

Similar to the foregoing experiments 24 female rats (Sprague Dawley) were randomized.
Number of groups: 2
Tumor: Yoshida-ascites (haemorrhagic)
Number of cells upon tumor inoculation: approx. 20,000

| Group A: | chondroitin polysulfate + | 12 mg/kg |
| | trypsin + | 6 mg/kg |
| | cyclophosphamide | 25 mg/kg |
| Group B: | control | |

Temporal sequence of the experiment:
Start of the therapy
(1. application of the therapeutically active substances 2 days after tumor transmission,
2. application: 3 days after tumor transmission,
3. application: 4 days after tumor transmission,
4. application: 5 days after tumor transmission,
5. application: 6 days after tumor transmission,
6. application: 7 days after tumor transmission).
Examination of the results 21 days after inoculation of the tumor.

A table 5 has been drawn up of the results.

TABLE 5

| Group with 12 animals | alive | free from a tumor in this group | dead | having a tumor |
|---|---|---|---|---|
| A | 11 | 11 | 1 | 0 |
| B | 0 | 0 | 12 | 12 |

No tumor could be found in the deceased animal of group A. The cause of death has not been cleared.

The results of the experiments show that the experimental animals exclusively treated with the cytostatic drug cyclophosphamide have died of the growth of the tumor in the course of the experiment similar to the control group. The experimental animals which have been given the cytostatic drug cyclophosphamide together with a glycosaminoglycan polysulfate and, in addition, trypsin have shown a significantly lengthened lifetime and partly, no growth of a tumor. When the groups B, D and E in experiment 1 as well as group A in experiment 3 and grou C in experiment 4 are compared with the groups A and C in experiment 1, group B in experiment 3, group A in experiment 4 and group A in experiment 5 the synergistic effect of the preparation according to the invention definitely results. Histological and cytochemical examinations carried out parallel to the animal experiments show that a largely selective effect to malignant cells can be obtained by the combination of the substances applied.

EXPERIMENT 6

60 female rats (Spraque Dawley) were classified into three groups (randomized).

Kind of tumor: Yoshida-ascites (haemorrhagic)
Number of cells of the Yoshida-ascites inoculation: approx. 20,000
Start of the therapy: 24 hours after inoculation
Group A: chondroitin polysulfate+cyclophosphamide+trypsin
Group B: chondroitin polysulfate+cyclophosphamide
Group C: control
Doses of the pharmacological active substances:
chondroitin polysulfate: 12 mg/per kg
cyclophosphamide (Endoxan): 24 mg/per kg
trypsin: 6 mg/per kg
Temporal sequence of the application:
Application of the aforementioned combination 24 hours after tumor inoculation. Further applications daily, on the whole, seven applications.

A table 6 has been drawn up of the results.

TABLE 6

| Group with 20 animals | alive | free from a tumor | dead | having a tumor |
|---|---|---|---|---|
| A | 19 | 19 | 1 | 0 |
| B | 12 | 12 | 8 | 7 |
| C | 0 | 0 | 20 | 20 |

This experiment was repeated. A table 7 has been drawn up of the results.

TABLE 7

| Group with 20 animals | alive | free from a tumor | dead | having a tumor |
|---|---|---|---|---|
| A | 18 | 18 | 2 | 0 |
| B | 11 | 11 | 9 | 7 |
| C | 1 | 0 | 19 | 19 |

As is especially shown by the results of experiment 6 a particular synergistic effect results from the combination of the cytostatic drug cyclophosphamide and chondroitin polysulfate and trypsin. It seems that a still now entirely understood reciprocity between the chondroitin polysulfate and trypsin entails an increased permeability of the malignant cells to the cytostatic drugs.

The experiments 3 to 6, in which the composition: chondroitin polysulfate+cyclophosphamide+trypsin was respectively compared with either chondroitin polysulfate+trypsin or cyclophosphamide or solely with a control or with chondroitin polysulfate+cyclophosphamide definitely prove that the combination according to the invention is suprisingly superior. Each of the experiments 3 to 6 individually shows that the chance of survival of the experimental animals is increased to a disproportionately high degree when the active substance combination of chondroitin polysulfate, trypsin and cyclophosphamide is administered.

In addition to the particular effectiveness to tumors having a great number of cells, it has been observed as has already been mentioned, that the aggravating secondary effects of the cytostatic drugs could be substantially reduced and this is an absolutely decisive innovation. In particular, younger women did either not or only slightly suffer from loss of hair. Furthermore, there was generally no sickness, no vomiting and no diarrhoea. What has to be particularly emphasized is the fact that the injuries of the medulla of a bone caused by the cytostatic drugs could be remarkably reduced.

What is claimed is:

1. A pharmaceutical composition in dosage unit form comprising from about 5 to 500 milligrams of a glycosaminoglycan polysulfate and a cytostatic drug in a quantity ratio of glycosaminoglycan polysulfate to cytostatic drug of from 10:1 to 1:10 by weight in association with a pharmaceutically acceptable carrier with the proviso that said glycosaminoglycan polysulfate is not heparin.

2. A pharmaceutical composition in dosage unit form comprising from about 5 to 500 milligrams of chondroitin polysulfate and a cytostatic drug in a quantity ratio of chondroitin polysulfate to cytostatic drug of from 10:1 to 1:10 by weight in association with a pharmaceutically acceptable carrier.

3. A composition according to claim 1 which further comprises trypsin in a ratio from 1:2 to 2:3 based on the total amount of the glycosaminoglycan polysulfate.

4. A composition according to claim 2 which further comprises trypsin in a ratio from 1:2 to 2:3 based on the total amount of the chondroitin polysulfate.

5. A method of inhibiting the growth of tumors in a mammal comprising administering to said mammal an effective antineoplastic amount of a composition containing glycosaminoglycan polysulfate and a cytostatic drug in a quantity ratio of glycosaminoglycan polysulfate to cytostatic drug of from 10:1 to 1:10 by weight; with the proviso that said glycosaminoglycan polysulfate is not heparin.

6. The method according to claim 5 in which the glycosaminoglycan polysulfate is chondroitin polysulfate.

7. The method according to claim 6 in which from 6 to 8 mg/kg trypsin is administered in conjunction with chondroitin polysulfate and cytostatic drug.

8. The method according to claim 5 in which from 6 to 8 mg/kg trypsin is administered in conjunction with the glycosaminoglycan polysulfate and cytostatic drug.

* * * * *